US008043287B2

(12) United States Patent
Conquergood et al.

(10) Patent No.: US 8,043,287 B2
(45) Date of Patent: *Oct. 25, 2011

(54) METHOD OF TREATING BIOLOGICAL TISSUE

(75) Inventors: Laura Conquergood, Mississauga (CA); Mark Leung, Toronto (CA); Subashini Chandran, Toronto (CA); Krishan Shah, Mississauga (CA); Frank Baylis, Beaconsfield (CA); Neil Godara, Mississauga (CA); Elizabeth Pyshnov, Toronto (CA); Amanda Martyn, Toronto (CA)

(73) Assignee: Kimberly-Clark Inc., Mississauga, Ontario (CA)

( * ) Notice: Subject to any disclaimer, the term of this patent is extended or adjusted under 35 U.S.C. 154(b) by 1138 days.

This patent is subject to a terminal disclaimer.

(21) Appl. No.: 11/128,342

(22) Filed: May 13, 2005

(65) Prior Publication Data

US 2005/0234445 A1    Oct. 20, 2005

Related U.S. Application Data

(63) Continuation-in-part of application No. 11/105,490, filed on Apr. 14, 2005, now abandoned, and a continuation-in-part of application No. 11/105,527, filed on Apr. 14, 2005, and a continuation-in-part of application No. 11/105,524, filed on Apr. 14, 2005, now Pat. No. 7,294,127, and a continuation-in-part of application No. 10/087,856, filed on Mar. 5, 2002, now Pat. No. 6,896,675, said application No. 11/105,527 is a continuation-in-part of application No. 10/087,856, said application No. 11/105,524 is a continuation-in-part of application No. 10/087,856.

(60) Provisional application No. 60/570,905, filed on May 14, 2004, provisional application No. 60/594,109, filed on Mar. 11, 2005.

(51) Int. Cl.
*A61B 18/12* (2006.01)

(52) U.S. Cl. ............... 606/41; 606/20; 606/31; 606/47; 606/49; 607/96; 607/101

(58) Field of Classification Search .............. 606/20–31, 606/41, 47, 49; 607/96, 101
See application file for complete search history.

(56) References Cited

U.S. PATENT DOCUMENTS 2,526,662 A    10/1950    Hipps et al.
(Continued)

FOREIGN PATENT DOCUMENTS

EP    0438242    7/1991
(Continued)

OTHER PUBLICATIONS

Case et al., "Changes of Intradisc Pressure Versus Volume Change", J. Clin. Laser Med & Surg., Jun. 1995, vol. 13(3), pp. 143-147.
(Continued)

*Primary Examiner* — Sam Yao
*Assistant Examiner* — Aaron Roane
(74) *Attorney, Agent, or Firm* — Dority & Manning, P.A.

(57) ABSTRACT

A treatment method is disclosed for treating a bodily tissue utilizing one or more steps of removal of material as well as one or more steps of energy delivery in order to effectively treat the bodily tissue. These mechanisms of treatment may beneficially be used to induce separate treatment effects, for example to treat both the symptoms and the underlying cause of a specific pathological condition. In addition, a specific application of the inventive method is described for using the inventive method to treat an intervertebral disc.

19 Claims, 2 Drawing Sheets

U.S. PATENT DOCUMENTS

| | | | |
|---|---|---|---|
| 3,477,423 A | 11/1969 | Griffith | |
| 3,732,858 A | 5/1973 | Banko | |
| 4,177,797 A | 12/1979 | Baylis et al. | |
| 4,369,788 A | 1/1983 | Goald | |
| 4,411,266 A | 10/1983 | Cosman | |
| 4,512,344 A | 4/1985 | Barber | |
| 4,600,014 A | 7/1986 | Beraha | |
| 4,649,919 A | 3/1987 | Thimsen et al. | |
| 4,699,154 A | 10/1987 | Lindgren | |
| 4,834,729 A | 5/1989 | Sjostrom | |
| 4,857,046 A | 8/1989 | Stevens et al. | |
| 4,883,458 A | 11/1989 | Shiber | |
| 4,907,589 A | 3/1990 | Cosman | |
| 4,958,625 A | 9/1990 | Bates et al. | |
| 4,979,939 A | 12/1990 | Shiber | |
| 5,002,553 A | 3/1991 | Shiber | |
| 5,027,792 A * | 7/1991 | Meyer | 600/104 |
| 5,074,841 A | 12/1991 | Ademovic et al. | |
| 5,084,052 A | 1/1992 | Jacobs | |
| RE34,056 E | 9/1992 | Lindgren | |
| 5,167,658 A | 12/1992 | Ensslin | |
| 5,183,054 A | 2/1993 | Burkholder et al. | |
| 5,201,729 A | 4/1993 | Hertzmann et al. | |
| 5,233,515 A | 8/1993 | Cosman | |
| 5,234,000 A | 8/1993 | Hakky et al. | |
| 5,277,201 A | 1/1994 | Stern | |
| 5,334,193 A | 8/1994 | Nardella | |
| 5,342,357 A | 8/1994 | Nardella | |
| 5,383,874 A | 1/1995 | Jackson et al. | |
| 5,383,884 A | 1/1995 | Summers | |
| 5,423,799 A | 6/1995 | Shiu | |
| 5,423,807 A | 6/1995 | Milder | |
| 5,423,811 A | 6/1995 | Imran et al. | |
| 5,433,739 A | 7/1995 | Sluijter et al. | |
| 5,437,662 A | 8/1995 | Nardella | |
| 5,458,596 A | 10/1995 | Lax et al. | |
| 5,484,400 A | 1/1996 | Edwards et al. | |
| 5,489,161 A | 2/1996 | Sugita et al. | |
| 5,520,682 A | 5/1996 | Baust et al. | |
| 5,536,267 A | 7/1996 | Edwards et al. | |
| 5,546,161 A | 8/1996 | Sakai et al. | |
| 5,569,242 A | 10/1996 | Lax et al. | |
| 5,569,284 A | 10/1996 | Young et al. | |
| 5,571,147 A | 11/1996 | Sluijter et al. | |
| 5,574,117 A | 11/1996 | Yoshida et al. | |
| 5,591,187 A | 1/1997 | Dekel | |
| 5,599,346 A | 2/1997 | Edwards et al. | |
| 5,603,221 A | 2/1997 | Maytal | |
| 5,647,871 A | 7/1997 | Levine et al. | |
| 5,651,780 A | 7/1997 | Jackson et al. | |
| 5,658,278 A | 8/1997 | Imran et al. | |
| 5,697,927 A | 12/1997 | Imran et al. | |
| 5,718,701 A | 2/1998 | Shai et al. | |
| 5,735,847 A | 4/1998 | Gough et al. | |
| 5,785,705 A | 7/1998 | Baker | |
| 5,800,481 A | 9/1998 | Loos | |
| 5,810,804 A | 9/1998 | Gough et al. | |
| 5,873,882 A | 2/1999 | Straub et al. | |
| 5,876,414 A | 3/1999 | Straub | |
| 5,906,612 A | 5/1999 | Chinn | |
| 5,916,163 A | 6/1999 | Panescu et al. | |
| 5,928,159 A | 7/1999 | Eggers et al. | |
| 5,957,922 A | 9/1999 | Imran | |
| 5,957,961 A | 9/1999 | Maguire et al. | |
| 5,968,062 A | 10/1999 | Thomas et al. | |
| 5,971,980 A | 10/1999 | Sherman | |
| 5,980,504 A | 11/1999 | Sharkey et al. | |
| 5,983,141 A | 11/1999 | Sluijter et al. | |
| 6,007,570 A | 12/1999 | Sharkey et al. | |
| 6,015,407 A | 1/2000 | Rieb et al. | |
| 6,016,809 A | 1/2000 | Mulier et al. | |
| 6,024,751 A | 2/2000 | Lovato et al. | |
| 6,033,399 A | 3/2000 | Gines | |
| 6,035,238 A | 3/2000 | Ingle et al. | |
| 6,051,019 A | 4/2000 | Dobak, III | |
| 6,053,912 A | 4/2000 | Panescu et al. | |
| 6,053,937 A | 4/2000 | Edwards et al. | |
| 6,063,085 A | 5/2000 | Tay et al. | |
| 6,073,051 A | 6/2000 | Sharkey et al. | |
| 6,074,386 A | 6/2000 | Goble et al. | |
| 6,074,389 A | 6/2000 | Levine et al. | |
| 6,074,412 A | 6/2000 | Mikus et al. | |
| 6,083,237 A | 7/2000 | Huitema et al. | |
| 6,095,149 A | 8/2000 | Sharkey et al. | |
| 6,099,514 A | 8/2000 | Sharkey et al. | |
| 6,109,268 A | 8/2000 | Thapliyal et al. | |
| 6,113,595 A | 9/2000 | Muntetmann | |
| 6,122,549 A | 9/2000 | Sharkey et al. | |
| 6,123,702 A | 9/2000 | Swanson et al. | |
| 6,126,682 A | 10/2000 | Sharkey et al. | |
| 6,136,014 A | 10/2000 | Sirimanne et al. | |
| 6,139,545 A | 10/2000 | Utley et al. | |
| 6,146,380 A | 11/2000 | Racz et al. | |
| 6,161,048 A | 12/2000 | Sluijter et al. | |
| 6,183,468 B1 | 2/2001 | Swanson et al. | |
| 6,197,021 B1 | 3/2001 | Panescu et al. | |
| 6,206,876 B1 | 3/2001 | Levine et al. | |
| 6,217,573 B1 | 4/2001 | Webster | |
| 6,228,080 B1 | 5/2001 | Gines | |
| 6,228,081 B1 | 5/2001 | Goble | |
| 6,237,569 B1 | 5/2001 | Stelzer et al. | |
| 6,238,387 B1 | 5/2001 | Miller, III | |
| 6,241,725 B1 | 6/2001 | Cosman | |
| 6,246,912 B1 | 6/2001 | Sluijter et al. | |
| 6,258,086 B1 | 7/2001 | Ashley et al. | |
| 6,259,952 B1 | 7/2001 | Sluijter et al. | |
| 6,261,311 B1 | 7/2001 | Sharkey et al. | |
| 6,264,650 B1 | 7/2001 | Hovda et al. | |
| 6,264,651 B1 | 7/2001 | Underwood et al. | |
| 6,273,861 B1 | 8/2001 | Bates et al. | |
| 6,277,112 B1 * | 8/2001 | Underwood et al. | 606/32 |
| 6,283,960 B1 | 9/2001 | Ashley | |
| 6,283,961 B1 | 9/2001 | Underwood et al. | |
| 6,290,715 B1 | 9/2001 | Sharkey et al. | |
| 6,293,943 B1 | 9/2001 | Panescu et al. | |
| 6,296,636 B1 | 10/2001 | Cheng et al. | |
| 6,309,387 B1 | 10/2001 | Eggers et al. | |
| 6,312,428 B1 | 11/2001 | Eggers et al. | |
| 6,325,806 B1 | 12/2001 | Fox | |
| 6,355,031 B1 | 3/2002 | Edwards et al. | |
| 6,355,032 B1 | 3/2002 | Hovda et al. | |
| 6,379,348 B1 | 4/2002 | Onik | |
| 6,391,026 B1 | 5/2002 | Hung et al. | |
| 6,416,508 B1 | 7/2002 | Eggers et al. | |
| 6,432,103 B1 | 8/2002 | Ellsberry et al. | |
| 6,451,015 B1 | 9/2002 | Rittman, III et al. | |
| 6,461,353 B1 | 10/2002 | Baker, Jr. et al. | |
| 6,464,695 B2 | 10/2002 | Hovda et al. | |
| 6,468,270 B1 | 10/2002 | Hovda et al. | |
| 6,468,274 B1 | 10/2002 | Alleyne et al. | |
| 6,478,793 B1 | 11/2002 | Cosman et al. | |
| 6,482,204 B1 | 11/2002 | Lax et al. | |
| 6,491,690 B1 | 12/2002 | Goble et al. | |
| 6,494,880 B1 | 12/2002 | Swanson et al. | |
| 6,500,172 B1 | 12/2002 | Panescu et al. | |
| 6,500,173 B2 | 12/2002 | Underwood et al. | |
| 6,506,189 B1 | 1/2003 | Rittman, III et al. | |
| 6,517,568 B1 | 2/2003 | Sharkey et al. | |
| 6,530,992 B1 | 3/2003 | Yank et al. | |
| 6,533,780 B1 | 3/2003 | Laird et al. | |
| 6,540,741 B1 | 4/2003 | Underwood et al. | |
| 6,544,195 B2 | 4/2003 | Wilson et al. | |
| 6,547,810 B1 | 4/2003 | Sharkey et al. | |
| 6,557,559 B1 | 5/2003 | Eggers et al. | |
| 6,558,381 B2 | 5/2003 | Ingle et al. | |
| 6,575,968 B1 | 6/2003 | Eggers et al. | |
| 6,575,969 B1 | 6/2003 | Rittman, Jr. et al. | |
| 6,584,360 B2 | 6/2003 | Francischelli et al. | |
| 6,587,731 B1 | 7/2003 | Ingle et al. | |
| 6,602,248 B1 | 8/2003 | Sharps et al. | |
| 6,604,003 B2 | 8/2003 | Fredricks et al. | |
| 6,613,047 B2 | 9/2003 | Edwards | |
| 6,620,155 B2 | 9/2003 | Underwood et al. | |
| 6,645,203 B2 | 11/2003 | Sharkey et al. | |
| 6,645,464 B1 | 11/2003 | Hainfeld | |
| 6,652,513 B2 | 11/2003 | Panescu et al. | |
| 6,673,023 B2 | 1/2004 | Pfluegger | |

| | | |
|---|---|---|
| 6,673,063 B2 | 1/2004 | Brett |
| 6,702,810 B2 | 3/2004 | McClurken et al. |
| 6,706,038 B2 | 3/2004 | Francischelli et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,723,091 B2 | 4/2004 | Goble et al. |
| 6,726,684 B1 | 4/2004 | Woloszko et al. |
| 6,726,685 B2 | 4/2004 | To et al. |
| 6,730,081 B1 | 5/2004 | Desai |
| 6,733,496 B2 | 5/2004 | Sharkey et al. |
| 6,736,815 B2 | 5/2004 | Ginn |
| 6,749,605 B2 | 6/2004 | Ashley et al. |
| 6,749,617 B1 | 6/2004 | Palasis et al. |
| 6,767,347 B2 | 7/2004 | Sharkey et al. |
| 6,772,012 B2 | 8/2004 | Ricart et al. |
| 6,783,532 B2 | 8/2004 | Steiner et al. |
| 6,796,982 B2 | 9/2004 | Carmel et al. |
| 6,821,276 B2 | 11/2004 | Lambrecht et al. |
| 6,827,716 B2 | 12/2004 | Ryan et al. |
| 6,832,996 B2 | 12/2004 | Woloszko et al. |
| 6,832,997 B2 | 12/2004 | Uchida et al. |
| 6,837,884 B2 | 1/2005 | Woloszko |
| 6,837,888 B2 | 1/2005 | Ciarrocca et al. |
| 6,846,314 B2 | 1/2005 | Shapira |
| 6,878,155 B2 | 4/2005 | Sharkey et al. |
| 6,896,675 B2 | 5/2005 | Leung et al. |
| 6,929,640 B1 | 8/2005 | Underwood et al. |
| 6,997,941 B2 | 2/2006 | Sharkey et al. |
| 7,097,641 B1 | 8/2006 | Arless et al. |
| 7,267,683 B2 | 9/2007 | Sharkey et al. |
| 7,282,061 B2 | 10/2007 | Sharkey et al. |
| 7,309,336 B2 | 12/2007 | Ashley et al. |
| 7,400,930 B2 | 7/2008 | Sharkey et al. |
| 7,593,778 B2 | 9/2009 | Chandran et al. |
| 2001/0001314 A1 | 5/2001 | Davison et al. |
| 2001/0025176 A1 | 9/2001 | Ellsberry et al. |
| 2001/0025177 A1 | 9/2001 | Eoloszko et al. |
| 2001/0032002 A1 | 10/2001 | McClurken et al. |
| 2002/0019626 A1 | 2/2002 | Sharkey et al. |
| 2002/0032441 A1 | 3/2002 | Ingle et al. |
| 2002/0072688 A1* | 6/2002 | Burbank et al. ............ 600/567 |
| 2002/0128641 A1 | 9/2002 | Underwood et al. |
| 2002/0138020 A1 | 9/2002 | Pflueger |
| 2002/0138091 A1 | 9/2002 | Pflueger |
| 2002/0188290 A1 | 12/2002 | Sharkey et al. |
| 2002/0188292 A1 | 12/2002 | Sharkey et al. |
| 2002/0193790 A1 | 12/2002 | Fleischman et al. |
| 2003/0158545 A1 | 8/2003 | Hovda et al. |
| 2004/0002746 A1 | 1/2004 | Ryan et al. |
| 2004/0059254 A1 | 3/2004 | Pflueger |
| 2004/0064137 A1 | 4/2004 | Pellegrino et al. |
| 2004/0176759 A1 | 9/2004 | Krishnamurthy et al. |
| 2004/0193151 A1 | 9/2004 | To et al. |
| 2004/0215181 A1 | 10/2004 | Christopherson et al. |
| 2005/0177209 A1 | 8/2005 | Leung et al. |
| 2005/0209530 A1 | 9/2005 | Pflueger |
| 2005/0234445 A1 | 10/2005 | Conquergood et al. |

FOREIGN PATENT DOCUMENTS

| | | |
|---|---|---|
| EP | 966920 | 12/1999 |
| EP | 1059067 | 12/2000 |
| EP | 1402838 | 3/2004 |
| IT | 1246197 | 11/1994 |
| WO | WO 98/17190 | 4/1998 |
| WO | WO 99/47058 | 9/1999 |
| WO | WO 01/45579 | 6/2001 |
| WO | WO 01/57655 | 8/2001 |
| WO | WO 01/62168 | 8/2001 |
| WO | WO 01/74251 | 10/2001 |
| WO | WO 03/073948 | 9/2003 |
| WO | WO 2005/110263 | 11/2005 |

OTHER PUBLICATIONS

Cripton et al., "A Minimally Disruptive Technique for Measuring Intervertebral Disc Pressure in Vitro: Application to the Cervical Spine", J. Biomech, Apr. 2001, vol. 34 (4), 545-549.

Freemont, "Nerve Ingrowth into Diseased Intervertebral Disc in Chronic Back Pain", The Lancet, 1997, 350, pp. 178-181.

McNally et al., "Development and Validation of a New Transducer for Intradiscal Pressure Measurement", J. Biomed. Eng., Nov. 1992, vol. 14(6) 495-498.

Panjabi et al., "Intrinsic Disc Pressure as a Measurement of Integrity of the Lumbar Spine", Spine, Aug. 1988, vol. 13(8) 913-977.

Wilke et al., "New in Vivo Measurements of Pressures in the Intervertebral Disc in Daily Life", Spine, Apr. 1999, vol. 15:24(8), 913-977.

* cited by examiner

METHOD OF TREATING BIOLOGICAL TISSUE

CROSS-REFERENCES TO RELATED APPLICATIONS

This application is a continuation-in-part of co-pending U.S. application Ser. No. 11/105,490, owned by Baylis Medical Company Inc., entitled "Bipolar tissue treatment system", filed Apr. 14, 2005, now abandoned, and a continuation-in-part of co-pending U.S. application Ser. No. 11/105,527, owned by Baylis Medical Company Inc., entitled "Electrosurgical device for treatment of tissue", filed Apr. 14, 2005 and a continuation-in-part of co-pending U.S. application Ser. No. 11/105,524, owned by Baylis Medical Company Inc., entitled "Electrosurgical tissue treatment method", filed Apr. 14, 2005, issued as U.S. Pat. No. 7,294,127, all of which are continuations-in-part of U.S. application Ser. No. 10/087,856, flied Mar. 5, 2002 now U.S. Pat. No. 6,896,675. This application also claims the benefit of U.S. provisional application No. 60/570,905, filed May 14, 2004 and of U.S. provisional application 60/594,109, filed Mar. 11, 2005.

TECHNICAL FIELD

The present invention relates to surgical methods of treating biological tissues and more specifically to surgical methods involving the delivery of energy or the removal of material.

BACKGROUND OF THE INVENTION

In many pathological conditions, unwanted material exists in the body. A few of the examples include: tumors growing at cancerous sites, excess fluid at a site of infection or injury, foreign biological material within a parasitic cyst, and herniation of a tissue, such as the nucleus pulposus of the intervertebral disc. Removal of the unwanted material, which can be performed by a variety of known methods, may relieve the symptoms of the pathology, for example by reducing the pressure of inflammation, or by shrinking a herniation. Removal alone, however, may not offer any protection against recurrence of the pathology. In the intervertebral disc, for example, herniation of the nucleus pulposus may be caused by weakening of or damage to the annulus fibrosus, the ring of tissue surrounding the nucleus; removal of herniated material of the nucleus pulposus may relieve pressure within the disc, but if the annular wall remains weak, herniation may recur.

Energy delivery is used to treat various pathologies and can, among many other uses, be used to kill cells, lesion tissue, disrupt neural function, and cause collagen contraction. For example, energy delivery may be used to treat fissures and tears in the annulus fibrosus of the intervertebral disc by causing collagen contraction and remodeling to tighten, strengthen, and weld the material of the annulus fibrosus. If the disc is herniated, however, material may need to be removed from the herniation or from other areas of the disc, in order to change the profile of the disc, and reduce the disc volume, prior to heating. In some cases, following delivery of energy to the tissue, for example, to kill tumor cells, it may be desirable to remove the necrosed tissue from the treatment site. Thus, it would be beneficial to have a treatment procedure incorporating both the removal of material as well as the delivery of energy during the course of a single procedure.

SUMMARY OF THE INVENTION

The present invention seeks to provide new and useful methods for treating bodily tissue, which incorporate both removal of material and delivery of energy.

According to a first aspect of the present invention, there is provided a treatment procedure for treating a bodily tissue having one or more treatment sites. The procedure comprises the steps of: inserting a tissue removal apparatus percutaneously into at least one of the one or more treatment sites; activating the tissue removal apparatus in order to remove tissue; inserting an energy delivery apparatus comprising at least two probes percutaneously into the tissue, with the probes being inserted into spaced apart treatment sites; and delivering energy via the energy delivery apparatus in a bipolar fashion such that the energy travels substantially between the at least two probes.

As a feature of the first aspect, the bodily tissue being treated may comprise an intervertebral disc, and the apparatus may further comprise a means of cooling the probes.

A second aspect of the present invention provides a treatment procedure for treating a bodily tissue, for example an intervertebral disc, having one or more treatment sites. The procedure comprises the steps of: inserting a tissue removal apparatus percutaneously into at least one of the one or more treatment sites, wherein the tissue removal apparatus comprises a mechanical conveyance apparatus that is structured to mechanically convey material to a location external to a patient's body; activating the apparatus in order to remove tissue; inserting an energy delivery apparatus percutaneously into at least one of the one or more treatment sites; and delivering energy via the energy delivery apparatus. As a feature of this aspect of the invention, energy may be delivered in a mode selected from the group consisting of a monopolar mode, a bipolar mode, a triphasic mode and a multi-polar mode According to a third aspect of the present invention, a treatment procedure is provided for treating an intervertebral disc having one or more treatment sites. The procedure comprises the steps of: percutaneously inserting a first apparatus into at least one of the one or more treatment sites of the disc, whereby the first apparatus is structured to remove material; activating the first apparatus in order to remove tissue from the intervertebral disc via mechanical conveyance; percutaneously inserting a second apparatus into at least one of the one or more treatment sites of the disc, whereby the second apparatus is structured to deliver energy; and delivering energy to the disc via the second apparatus.

As an additional feature of any of the three aspects described above, the treatment procedure may further comprise the steps of: measuring a parameter selected from the group consisting of a temperature and an electrical impedance; and controlling the delivery of energy in response to a measured parameter. Furthermore, at least one of the apparatuses used in a procedure of the present invention (e.g. for delivering energy or removing material) may comprise a marker selected from the group consisting of a radiopaque marker, a visual marker and a tactile marker.

As a further feature, the treatment procedures of the present invention may further comprise a step of measuring a tissue parameter in order to determine the efficacy of said treatment procedure. Alternatively or in addition, the treatment procedure may further comprise the steps of: measuring the pressure exerted by the bodily tissue on the apparatus used to remove tissue; and controlling the removal of tissue in response to a measured pressure.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

DEFINITIONS

In the context of the present invention, the term 'probe' may be used to describe any elongate apparatus that may be percutaneously inserted into a patient's body. These apparatuses include but are not limited to catheters, cannulae and electrosurgical probes. The apparatus can be flexible, stiff or semi-rigid and the invention is not limited in this regard. Similarly, any references to an introducer, sheath, cannula or other medical apparatus is not intended to be limited to a specific apparatus. Rather, any apparatus that may accomplish the same function as these apparatuses is intended to be within the scope of the present invention.

Overview of Method

In general, the invention disclosed herein is a method of treating a tissue involving a step of removing material from a patient's body to produce one treatment effect and a step of delivering a form of energy to the body to produce a second treatment effect. In some embodiments, for example, the step of removing material is performed to relieve the symptoms or effects of a particular condition, while the step of delivering energy is performed to treat the condition itself or to prevent or diminish future recurrence of symptoms. A variety of means for removing material from the body may be employed, and each means may be accomplished with one or more of a variety of apparatuses. Similarly, the means for delivering energy and the apparatuses used to deliver energy may vary, depending, for example, on the type of energy being applied. The step of removing material and the step of delivering energy may be performed in any order, with any number of repetitions, may be performed coincidentally or separately, and may be performed in conjunction with other procedures.

Methods of Removing Material

In some embodiments, the step of removing material from the body involves the removal of biological material including, but not limited to: tissue, blood, lymph, synovial fluid, vitreous or aqueous humor, cerebrospinal fluid, and other materials created through biological processes (for example, arterial plaque, or calcified deposits). However it is to be understood that the methods and means discussed below may be applied to any material. The means for removing material may include, for example: mechanical means, chemical means, means involving the delivery or removal of energy, or any combination of the above.

Removing material from a treatment site may have at least one beneficial effect including, but not limited to: reducing pressure within the material (or tissue, if the material comprises a tissue), reducing pressure exerted by the material or tissue on another material or tissue, removing diseased, deformed, mutated or otherwise pathologically undesirable material, allowing access to a treatment site to perform a procedure such as delivering energy, or shaping damaged or malformed tissue.

Removing material may include, in some embodiments, the steps of: isolating, detaching, or dislodging the material, and withdrawing the material from the body. In some other embodiments, step of removing material involves the destruction of the material, or its transformation to another state or form, and the withdrawal of any new material resulting from said destruction or transformation. Some embodiments involve both the isolation, detachment, or dislodgement of material and the destruction or transformation of material. Some materials, for example some fluids, may be withdrawn from the body without previously having to be manipulated in any way.

Mechanical means for isolating, detaching or dislodging material include, but are not limited to, one or more of: coring, grasping, cutting, drilling, twisting, abrading, applying positive pressure to push, and applying negative pressure to pull. Material may be mechanically destroyed or transformed by, for example, one or more of: being pulled apart, being compressed, being cut, or being abraded. Mechanical means for withdrawing biological material include, but are not limited to: drawing the material out of the body using negative pressure, pushing the material from the body using positive pressure, encasing or holding a grasped, cored, or otherwise physically constrained quantity of biological material within a portion of a apparatus and removing said apparatus from the tissue, using a mechanical conveyance apparatus to mechanically carry material to a location external to the body without withdrawing the apparatus from the body, and allowing the biological material to vent or drain (in some cases where the biological material is liquid (or viscous semisolid) or gaseous).

In some embodiments, the steps of detaching or dislodging material, and destroying or transforming material, where these steps are used, may be performed using chemical means, including, but not limited to: enzymes, oxidizing agents, reducing agents, acids, bases, and toxins. Chemical means may also be used to facilitate removal of biological material from the body, for example, by binding or chelating the material in a manner that may increase the ease of its removal.

In some other embodiments, the steps of detaching or dislodging material, and destroying or transforming material, where these steps are used, may be performed using means for delivering energy. Energy may be delivered in order to, for example: cut, perforate, desiccate, vaporize, liquefy, penetrate, ablate, or increase or decrease the viscosity of biological material. Removal of energy can also be used for the above steps, for example, in the form of cryogenic tissue cutting, perforation, or ablation. In some embodiments, freezing of biological material by removal of energy can destroy the tissue and may also be used in order to facilitate the removal of the biological material, for example, by coring.

This step of the method of the present invention, removing biological material from a treatment site of a body, may be performed using a wide variety of apparatuses. For the purposes of clarity, any such apparatuses will be referred to throughout this specification as tissue removal apparatuses. Apparatuses that can be used in the mechanical removal of tissue may include apparatuses with one or more of: blades, forceps (or other grasping elements), drills, augers, suction apparatuses, needles, solid abrasive structures, lumens for delivering an abrasive fluid or other fluid under pressure, or other cutting or piercing components. Any of the above components may oscillate or vibrate or otherwise move in such a way that enhances their function.

One particular embodiment uses an auger, or other screw-like apparatus, within a sheath to isolate and remove biological material, as described, for example, in U.S. Provisional Patent Application Ser. No. 60/594,109 to Conquergood et al., filed Mar. 11, 2005, which is incorporated by reference herein. When the auger is placed in contact with the biological material, and is rotated, a portion of the biological material may be drawn into the sheath, according to the principle of the Archimedean screw. Rotation of the auger may continue to draw biological material from the treatment site as long as the auger is in contact with biological material. The benefit of this embodiment, which uses a mechanical conveyance apparatus, is that it provides means for removing tissue without requiring negative pressure or suction. Its mechanical nature allows for potential use in a wider range of treatment facilities.

Another embodiment uses an apparatus for removing tissue which benefits from being operable without an external means of creating suction, but which may be limited in which biological materials can be removed by the viscosity of the materials present. The apparatus comprises an elongated shaft open at the distal end and having a one-way valve on an outer surface of the shaft, which vents to a tube or other external shaft component, and a plunger-like component which completely obstructs the shaft proximal to the valve, and which is moveable with the application of mechanical force (for example, by being connected to a rigid rod that is moveable by a motor). The plunger is moved in two strokes. In one stroke, the plunger is drawn backwards, drawing biological material into the shaft. In the next stroke, the plunger is pushed forwards, expelling air within the shaft through the valve. This sequence of steps (which may begin with either step) is repeated until the shaft is full or until the desired volume of biological material has been withdrawn.

Apparatuses that can be used to remove biological material with chemical means, according to the method of the invention may include one or more of: lumens for delivering a chemical means to the treatment site, connectors for attaching syringes or other delivery apparatuses, pumps or a fluid delivery system for controlling the delivery of chemical means, or specialized tubing or nozzles to direct the delivery of chemical means or to isolate or combine multiple chemical means.

Apparatuses that can be used to deliver energy according to the method of the current invention may include probes with one or more of: electrodes for delivering electromagnetic energy to the tissue, elements for delivering thermal energy to the tissue, lumens for the circulation or release of a heated or electrically-conducting fluid, or optical components. In embodiments where one or more electrodes are used to deliver energy, said electrodes may be configured to deliver energy in a monopolar configuration, from one or more active electrodes to a reference electrode elsewhere on or in the body, or in a bipolar configuration, from one electrode to another of relatively similar size (as compared to a reference electrode used in a monopolar treatment, which is relatively larger than an active electrode). Bipolar energy delivery may involve delivery of energy between electrodes on a single probe or other single apparatus inserted into the body, or between probes or apparatuses. Additionally, in some embodiments, energy may be delivered in a manner whereby the path of energy or configuration of the system is dynamically changed during the procedure, for example, by altering the resistance between a generator and various electrical components such as one or more active electrodes and a reference electrode, so that the amount of energy traveling to the between the conductive components is modulated. Apparatuses used to remove energy from the biological material may include one or more of: lumens to deliver a cooling or endothermic fluid to the treatment site, or electrothermal cooling apparatuses.

Methods of Delivering Energy

In some embodiments, the step of delivering energy involves the delivery of energy to a biological material, as described above, however it is understood that the methods and means discussed below may be applied to any material. Energy delivered may include, but is not limited to: thermal energy, electromagnetic energy, ultrasonic energy and optical or laser energy. The energy may be delivered directly to the biological material, for example, by passing an electrical current through the biological material, or may be transmitted to the material, for example, by conduction. Alternatively, energy may be delivered by chemical means, for example, by introducing an exothermic or electrically conductive compound to the treatment site.

Depending on the biological material being treated, energy delivery may have a number of beneficial effects including, but not limited to: tightening, strengthening or otherwise modifying the structure of the biological material, cauterizing blood vessels, sealing tissue, ablating biological material or tissues (for example, neural tissue) to a degree that impedes its function, promoting an immune response, promoting a healing response, promoting the synthesis of heat-shock proteins, destroying unwanted tissue, or killing infective or infected cells.

The step of delivering energy may involve single or multiple applications, may be interrupted or pulsed, may be performed before or after other procedures, and may involve the application of one or more forms of energy.

Apparatuses used to deliver energy, according to the method of the present invention, may include one or more of a variety of components as listed above where apparatuses used for delivering energy to remove biological material are mentioned. In addition, apparatuses used to deliver energy for any step of the present method may additionally include a cooling means in order to cool the tissue immediately surrounding the apparatus, allowing more energy to be delivered into the tissue and thus potentially increasing the volume of biological material treated.

In one particular embodiment of the present invention, energy is delivered using a system with two probes capable of delivering radiofrequency energy in a bipolar configuration, for example as described in U.S. patent application Ser. No.

11/105,490 to Leung et al., entitled "Bipolar tissue treatment system" and filed Apr. 14, 2005, which is incorporated by reference herein. The probes are inserted into the treatment site at a predetermined distance apart, and energy is delivered between the probes. Cooling fluid is circulated through both probes cooling the biological material surrounding the probes and allowing power to be supplied such that a lesion can form in the biological material substantially between the probes, but without searing or otherwise causing unwanted damage to the tissue surrounding the probes.

Variants and Combinations

In the method of the present invention, comprising the steps of removing material from a treatment site in a body and delivering energy to the treatment site, the steps may be performed in any order, including coincidentally, and may be repeated one or more times. In some embodiments, energy is delivered by a first apparatus, or a first component of a apparatus concurrent with material being removed by a second apparatus or a second component of the first apparatus. In some other embodiments, one apparatus or a component of a apparatus delivers energy to remove material, as described in the first section above, with the energy delivery having a second beneficial effect (for example, thermally inducing tissue contraction) as described in the second section above.

Material may, in some embodiments, be removed prior to energy being delivered in order, as mentioned above, to provide access to the treatment site, or to remove diseased or damaged tissue before delivering energy to treat the cause of the disease or damage. In other embodiments, energy may be delivered to treat material at the treatment site first, followed by tissue removal in order to remove some heated material, for example, charred tissue or denatured proteinaceous material. In one embodiment, where the apparatus or apparatuses used to deliver energy are inserted percutaneously, the steps of delivering energy and removing tissue (performed multiple times, simultaneously, or in either order) are followed by a step of delivering energy in order to seal or promote sealing of at least a part of the path of entry of the apparatus or apparatuses.

Apparatuses used to perform the method of the current invention, may comprise any one or more of the components listed above, on one or on multiple apparatuses, and may also have additional features including, but are not limited to: means for steering or navigating at least a portion of a apparatus (e.g. a cable or system of cables for actuating a curve in the distal end of a apparatus), means for facilitating the insertion of the apparatus, a stylet or other occluding means to prevent material from entering a apparatus during insertion, one or more lumens for the delivery or circulation of fluid, one or more apertures for allowing fluid to exit a apparatus, one or more sensing means for sensing temperature, pressure, impedance or another parameter, means for communicating sensory, status, or procedural information to a user or to a processor or controller (including wireless means), and one or more markers such as radiopaque, tactile, or visual markers.

The method of the current invention may also comprise additional steps, which may be performed in any sequence with respect to, or concurrently with, the steps of removing material and delivering energy. Additional steps may include, but are not limited to, one or more of: measuring a parameter of the material at the treatment site (e.g. temperature, impedance and/or pressure) or of any apparatuses or components; visually displaying information regarding measurements made, apparatus status or progression of method steps; automatically altering the treatment in response to any measured parameters of the material or apparatuses; electrically stimulating a tissue or other material at the treatment site in the body; sensing the electrical, muscular, or other biological reaction to electrical stimulation in the tissue; evoking and sensing the somato-sensory evoked potential (SSEP) of a neural tissue; adding material to the tissue site (e.g. anesthetics or other pharmaceuticals, sealants, electrically conducting fluid, and cooling fluid); visualizing the treatment site; and repositioning, replacing or internally navigating a apparatus.

In one exemplary embodiment, the step of delivering energy may be preceded and followed by measurement of the impedance of the material in the vicinity of the treatment site. This measurement is beneficial because it can provide information on the impact or effect of the energy delivery on the material. Frequently, if a lesion has been created in a tissue or other biological material, the impedance will be higher than in unlesioned tissue.

In another, non-exclusive, embodiment temperature may be measured during the energy delivery step. Measurement of temperature may beneficially provide information on the impact or effect of energy delivery on the material being measured. This temperature information may then be used in a manual or automatic feedback control system, for example, allowing the energy delivery to be increased if the temperature is below the range required for producing the desired effect, or allowing the energy delivery to be decreased if the temperature is above a point at which unwanted effects are likely to occur.

Specific Application of the Method for Treating an Intervertebral Disc

The intervertebral disc is a soft tissue located between adjacent vertebral bodies in a vertebral column. The disc comprises a central, gelatinous nucleus pulposus encircled by a tough, fibrous annulus fibrosis. The disc separates vertebral bodies and it allows for the mechanical motion of the vertebral column. The structure of the disc, as described above, gives it the necessary strength to sustain weight from the vertebrae, allows it to be deformable to accommodate movement of vertebrae and allows it to be strong enough to avoid injury during movement. Thus, any changes to a disc can affect the vertebral column activity significantly.

The annulus fibrosis is composed of layers of fibrocartilage, in which collagen fibres arranged in concentric rings run obliquely between vertical bodies. The annulus fibrosis surrounds the gelatinous nucleus pulposus. The nucleus pulposus plays an important role in the nutrition of the disc and in the biomechanical motion of the vertebral column by absorbing shock and increasing flexibility. It is normally under pressure and is contained in an ovoid cavity formed laterally by the annulus fibrosis and bounded by cartilaginous end plates covering adjacent vertebrae.

Disorders of the disc can result in debilitating pain and can cause disruption of daily activities. Common disorders of the disc include localized tears and fissures in the annulus fibrosis, contained, extruded or sequestered disc herniations and chronic circumferential bulging of the intervertebral discs. In some cases, the posterior region of the disc ruptures, thereby exerting pressure on adjacent nerve fibres and resulting in pain. Another cause of pain can be chemically induced when the disc is herniated severely enough that the nucleus pulposus contacts the nerve fibres. Chemicals in the nucleus pulposus can cause pain when they come in contact with certain nerve structures.

In one particular application of the present invention, the method can be used to treat herniation, tearing or compression of the intervertebral disc. Removing material from the disc can relieve pressure within the disc and can reduce the disc volume, potentially shrinking herniations, while delivery of energy may serve to remodel collagen, thereby tightening the disc, seal fissures, or damage or destroy neural tissue that is growing into fissures in the disc or that is being undesirably stimulated by contact with the contents of the nucleus pulposus.

Figure 1A:
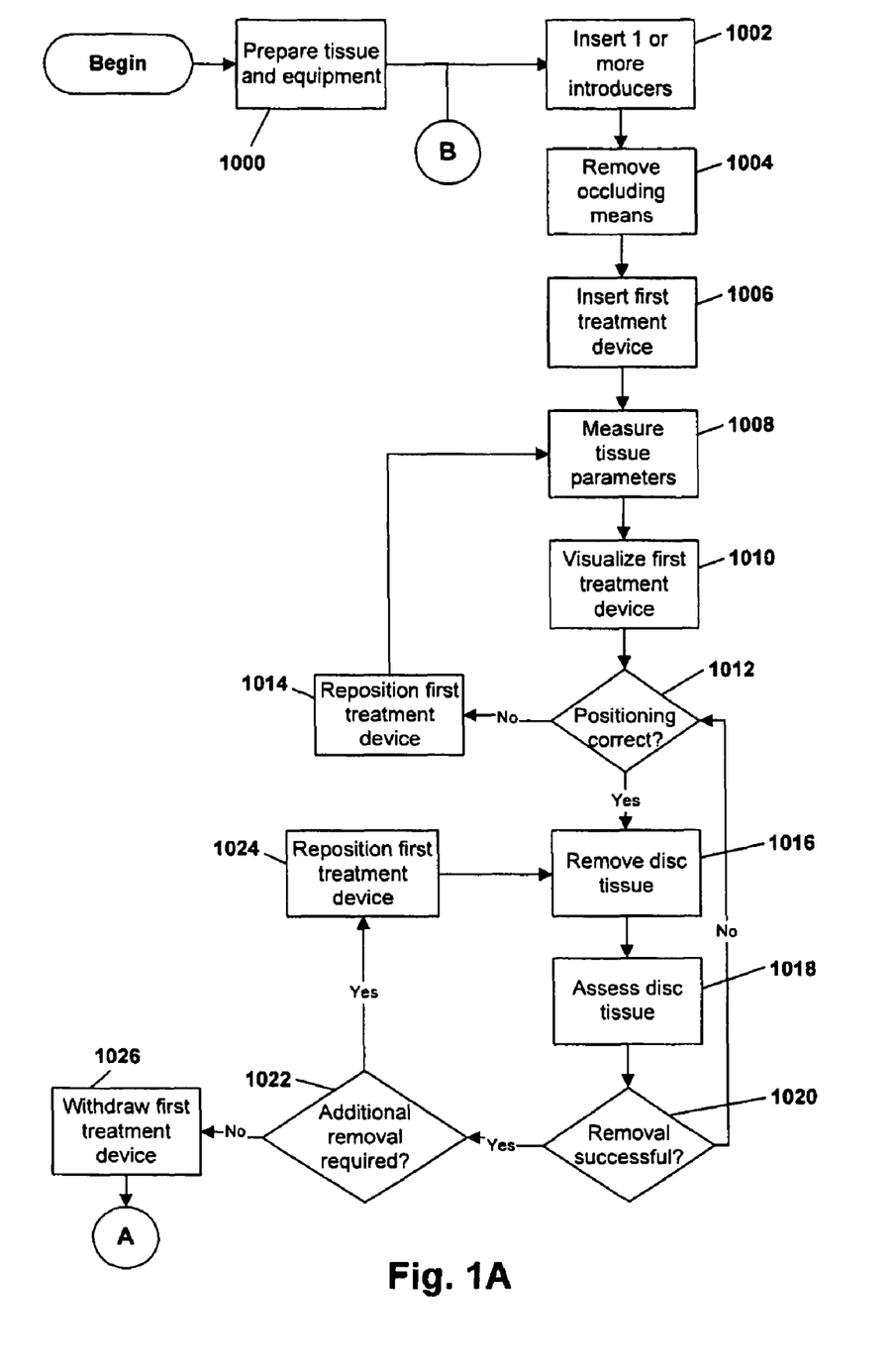
FIGS. 1A and 1B are first and second partial flowcharts, jointly illustrating a method for treating an intervertebral disc, according to one particular embodiment of the method of the current invention.
Figure 1B:
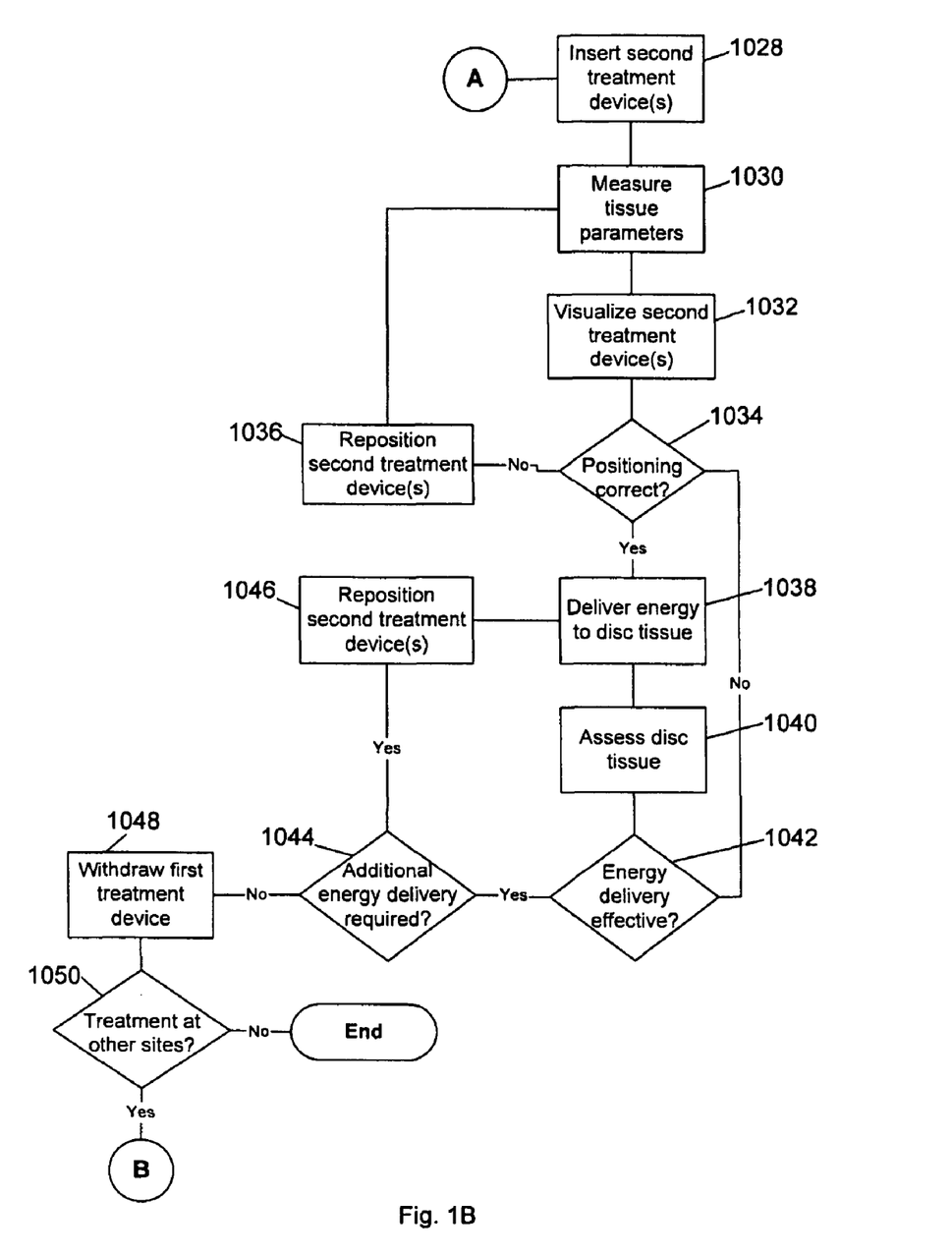

The method of the invention, according to this particular embodiment, may be practiced as illustrated in FIGS. 1A and 1B:

At step 1000 (FIG. 1A), the patient and equipment are prepared, which may include initial monitoring and measuring of tissue or apparatus parameters, and may include visualization of the treatment site using, for example, fluoroscopy. At step 1002 of at least one introducer apparatus, occluded with a stylet (or other occluding means), is inserted percutaneously into the disc adjacent at least one treatment site (e.g. within the nucleus, within the annulus, within or adjacent a disc herniation, within or adjacent a fissure). The insertion of the introducer or introducers may be aided by, for example, impedance monitoring or fluoroscopic imaging. Step 1004 comprises removal of the occluding means from the one or more introducers, followed by insertion of a first treatment apparatus, comprising a hollow, elongated shaft containing an auger, into the introducer shaft at step 1006. Measurement of one or more parameters of the intervertebral disc tissue (e.g. pressure, impedance, temperature) occurs at step 1008, using sensors located on the first treatment apparatus. Step 1010 comprises visualizing the positioning of the first treatment apparatus in order to ensure that the distal tip of the apparatus is in contact with at least a portion of tissue to be removed. At step 1012, the position of the apparatus is assessed and, if the position is incorrect, repositioning, navigating or steering the first treatment apparatus may occur at step 1014, via the NO branch. Alternatively, if the position of the apparatus is correct, the procedure may proceed via YES branch to step 1016, wherein disc tissue is removed by activating the first treatment apparatus, whereby the auger is rotated, drawing at least a portion of the material of the intervertebral disc into the shaft of the apparatus. Assessment of intervertebral disc tissue occurs at step 1018 using at least one of measurement of tissue parameters and visualization of the treatment site, in order to evaluate the effectiveness of tissue removal in achieving desired results. If the removal of tissue was unsuccessful (via NO branch of step 1020), the positioning of the apparatus may be re-assessed at step 1012. Alternatively, if the removal of tissue was successful (via YES branch of step 1020), and removal of additional material is required (via YES branch of step 1022), the apparatus may be repositioned at step 1024 in order to access another location at the treatment site (for example by steering the apparatus using a guide wire). Alternatively, if no further material is to be removed (via NO branch of step 1022), the first treatment apparatus may be withdrawn at step 1026 and the method proceeds via A to step 1028.

At step 1028 (FIG. 1B), one or more second treatment apparatuses, comprising electrically-conductive probes, are inserted into one or more of the introducers. Measurement of one or more parameters of intervertebral disc tissue adjacent the one or more second treatment apparatuses occurs at step 1030. Step 1032 comprises visualizing the positioning of the second treatment apparatus or apparatuses in order to ensure that they are positioned at the desired treatment site. Repositioning, navigating or steering one or more of the second treatment apparatuses, if necessary, occurs at step 1036 via the NO branch of step 1034. Alternatively, if the positioning is correct, energy is delivered in a monopolar configuration, or in a biopolar configuration at step 1038, via the YES branch of step 1034. In some embodiments, at least one parameter of the intervertebral disc tissue (e.g. temperature) is monitored in conjunction with the step of delivering energy. At step 1040, the disc tissue is assessed using at least one of measurement of tissue parameters and visualization of the treatment site, in order to evaluate the effectiveness of the energy delivery in achieving the desired results. If the assessment shows that energy delivery was not effective at NO branch of step 1042, the positioning of the apparatus may be re-assessed at step 1034. Alternatively if the assessment shows that the energy delivery was effective (at YES branch of step 1042), and additional energy delivery is required (YES branch of step 1044), one or more second treatment apparatuses may be repositioned at step 1046 in order to access another location at the treatment site. If no further energy delivery is required (NO branch of step 1044), the one or more second treatment apparatuses may be withdrawn at step 1048. If treatment is required at another treatment site (YES branch of step 1050), one or more introducers may be inserted at step 1002 (via B) in order to access the other treatment site. Alternatively, if treatment is not required at another treatment site, the method is complete (via NO branch of step 1050.

Alternatives to the above embodiment include, but are not limited to, embodiments in which measurement steps 1008, 1018, 1030 and 1040 involve the use of measurement apparatuses separate from, rather than integral to, the first and second treatment apparatuses. In some embodiments, steps using a first treatment apparatus, 1006-1026 may be performed coincident to or following steps using a second treatment apparatus, 1028-1048. Furthermore, as has been mentioned, the tissue removed may comprise any tissue of the intervertebral disc, including nuclear or annular tissue. Similarly, energy may be delivered to any desired region of the disc. In one embodiment, the tissue that is removed is nuclear tissue, while energy is delivered to both the annulus and the nucleus.

Various other applications of the method of the present invention exist, including, for example, arthroscopic or tumor ablation applications, and the description of the above embodiment is not intended to limit the present invention to one specific application.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A treatment procedure for treating bodily tissue having one or more treatment sites, comprising the steps of:
   (i) percutaneously inserting a tissue removal apparatus into at least one of said one or more treatment sites;
   (ii) activating said tissue removal apparatus to remove tissue;
   (iii) percutaneously inserting an energy delivery apparatus into at least one of said one or more treatment sites; and
   (iv) delivering energy via said energy delivery apparatus;
   wherein said energy delivery apparatus comprises at least two separate probes independently positionable relative to one another and wherein the step of inserting the probes comprises inserting said at least two probes into spaced apart treatment sites and wherein said energy is delivered in a bipolar fashion between said at least two probes.

2. The treatment procedure of claim 1, wherein said bodily tissue comprises an intervertebral disc.

3. The treatment procedure of claim 1, wherein said energy delivery apparatus further comprises a means of cooling said probes.

4. The treatment procedure of claim 1, further comprising the steps of:
   (v) measuring a parameter selected from the group consisting of a temperature and an electrical impedance; and
   (vi) controlling the delivery of energy in response to a measured parameter.

5. The treatment procedure of claim 1, wherein at least one of said energy delivery apparatus and said tissue removal apparatus comprises a marker selected from the group consisting of a radiopaque marker, a visual marker and a tactile marker.

6. The treatment procedure of claim 1, further comprising a step of measuring a tissue parameter in order to determine the efficacy of said treatment procedure.

7. The treatment procedure of claim 1, further comprising the steps of:
   (v) measuring the pressure exerted by said bodily tissue on said tissue removal apparatus; and
   (vi) controlling the removal of tissue in response to a measured pressure.

8. The treatment procedure of claim 3, wherein said means of cooling said probes comprises means for internally cooling said probes.

9. A treatment procedure for treating bodily tissue having one or more treatment sites, comprising the steps of:
   (i) percutaneously inserting a tissue removal apparatus into at least one of said one or more treatment sites;
   (ii) activating said tissue removal apparatus to remove tissue;
   (iii) percutaneously inserting an energy delivery apparatus having at least two separate probes independently positionable relative to one another into at least one of said one or more treatment sites by inserting said at least two probes into spaced apart treatment sites; and
   (iv) delivering energy via said energy delivery apparatus in a bipolar fashion between said at least two probes;
   wherein said tissue removal apparatus comprises a mechanical conveyance apparatus and wherein said mechanical conveyance apparatus is located within a sheath and is structured to mechanically convey material to a location external to a patient's body without suctioning the material to the location.

10. The treatment procedure of claim 9, wherein said bodily tissue comprises an intervertebral disc.

11. The treatment procedure of claim 9, further comprising the steps of:
   (v) measuring a parameter selected from the group consisting of a temperature and an electrical impedance; and
   (vi) controlling the delivery of energy in response to a measured parameter.

12. The treatment procedure of claim 9, wherein at least one of said energy delivery apparatus and said tissue removal apparatus comprises a marker selected from the group consisting of a radiopaque marker, a visual marker and a tactile marker.

13. The treatment procedure of claim 9, further comprising a step of measuring a tissue parameter in order to determine the efficacy of said treatment procedure.

14. The treatment procedure of claim 9, further comprising the steps of:
   (v) measuring the pressure exerted by said bodily tissue on said tissue removal apparatus; and
   (vi) controlling the removal of tissue in response to a measured pressure.

15. A treatment procedure for treating an intervertebral disc having one or more treatment sites, comprising the steps of:
   (i) percutaneously inserting a first apparatus structured to remove material into at least one of said one or more treatment sites of said intervertebral disc;
   (ii) activating said first apparatus to remove tissue from said intervertebral disc;
   (iii) percutaneously inserting a second apparatus having at least two separate probes independently positionable relative to one another structured to deliver energy into at least one of said one or more treatment sites of said intervertebral disc inserting said at least two probes into spaced apart treatment sites; and
   (iv) delivering energy via said second apparatus in a bipolar fashion between said at least two probes to said intervertebral disc;
   wherein the tissue is removed via a mechanical conveyance without suctioning.

16. The treatment procedure of claim 15, further comprising the steps of:
   (v) measuring a parameter selected from the group consisting of a temperature and an electrical impedance; and
   (vi) controlling the delivery of energy in response to a measured parameter.

17. The treatment procedure of claim 15, wherein at least one of said first apparatus and said second apparatus comprises a marker selected from the group consisting of a radiopaque marker, a visual marker and a tactile marker.

18. The treatment procedure of claim 15, further comprising a step of measuring a tissue parameter in order to determine the efficacy of said treatment procedure.

19. The treatment procedure of claim 15, further comprising the steps of:
   (v) measuring the pressure exerted by said bodily tissue on said first apparatus; and
   (vi) controlling the removal of tissue in response to a measured pressure.

* * * * *